United States Patent [19]

Silén

[11] Patent Number: 4,747,409
[45] Date of Patent: May 31, 1988

[54] THERMAL VASCULAR DILATOR

[75] Inventor: Per-Olof Silén, Knivsta, Sweden

[73] Assignee: Teknikhuset Swetron AB, Jarfalla, Sweden

[21] Appl. No.: 14,060

[22] PCT Filed: May 7, 1986

[86] PCT No.: PCT/SE86/00215
§ 371 Date: Jan. 7, 1987
§ 102(e) Date: Jan. 7, 1987

[87] PCT Pub. No.: WO86/06622
PCT Pub. Date: Nov. 20, 1986

[30] Foreign Application Priority Data

May 7, 1985 [SE] Sweden .................................. 8502248

[51] Int. Cl.⁴ .............................................. A61F 7/00
[52] U.S. Cl. .................................. 128/402; 128/303.1; 128/82.1
[58] Field of Search ..................... 128/402, 82.1, 87 R, 128/375, 379, 381, DIG. 15, 68.1, 399, 341, 303.11, 362, 303.1; 604/114, 113; 219/211, 535, 527, 528, 534, 536

[56] References Cited

U.S. PATENT DOCUMENTS

| 1,703,993 | 3/1929 | Denton ................................. 128/375 |
| 1,875,261 | 8/1932 | Pot ....................................... 128/375 |
| 1,968,015 | 7/1934 | Cooke et al. ......................... 128/375 |
| 2,298,298 | 10/1942 | Joy et al. ............................. 219/211 |
| 2,429,110 | 10/1947 | Staloch ................................ 128/402 |
| 2,617,916 | 11/1952 | Neidnlg ............................... 219/535 |
| 3,232,289 | 2/1966 | Zimmerman ...................... 128/87 R |
| 4,107,509 | 8/1978 | Scher et al. ........................ 128/379 |
| 4,215,687 | 8/1980 | Shaw .......................... 128/DIG. 15 |

FOREIGN PATENT DOCUMENTS 2708595 8/1978 Fed. Rep. of Germany ...... 219/535

Primary Examiner—Richard C. Pinkham
Assistant Examiner—Mark S. Graham
Attorney, Agent, or Firm—Pollock, Vande Sande & Priddy

[57] ABSTRACT

A body-attached device for dilating blood vessels. An elongated, rigid channel-shaped member receives the under side of a body extremity such as the forearm. The inside of the member carries a sleeve which is adapted to be wrapped over the top side of the arm and retained in place by Velcro tabs. The sleeve contains electric resistance heating elements and is in several sections separately wrappable around the arm. The forward end of the elongated member has a handle bar to be gripped by the user's hand.

5 Claims, 1 Drawing Sheet

THERMAL VASCULAR DILATOR

FIELD OF THE INVENTION

The present invention concerns a device for dilating extremity blood vessels by thermal treatment. Hereinafter such device is referred to as a thermal vascular dilator.

BACKGROUND OF THE INVENTION

A great part of medical research is based on collecting numerous blood samples from patients and healthy test persons. This necessitates insertion of sampling and infusion cannulas in peripheral arm veins. Tolerance tests are also carried out in routine medical services and form the basis of many endocrine analyses. Also our entire hormone diagnostics is based on venipuncture. Since not all patients have vessels perfect to puncture, it has been necessary to employ specialized test nurses well trained in puncturing and managing the insertion of test needles in a patient. Many patients with endocrine diseases have bad vessels. Such diseases are, e.g., Cushing's syndrome, Addison's disease, diabetes, hypofysial malfunctions such as obesity, and so on. It has become routine therefore, to utilize commonly available heat pads for heating of an arm before a puncturing attempt is made. In this way the circulation is increased and a better filling of the vessels is obtained, which facilitates cannula insertion. The existing heat pads, however, are not adapted to this purpose. They easily slip off and the heating efficiency is bad. For certain purposes these heat pads are quite unsuitable, e.g., when there is a need for arterialization of venous blood. The thermostat used in the pads periodically switches the current off; this results in great temperature fluctuations and consequently unpredictable variations in the arterialization of the blood.

There is a need, thus, for a suiatable thermal vascular dilator having a stable temperature steplessly variable between 27° C. and 50° C. Such a device would be useful in all instances of public medical care involving blood sampling as well as in polyclinical and institutional medical care. A vessel dilator would be a great help for all nurses who often have to make venipunctures on patients having bad vessels. It is commonly known in medical circles that this is a frequent problem. An efficient remedy should save much time and thereby release resources needed in other areas of the medical service.

It would be particularly valuable if all acute surgeries and intensive care surgeries could be equipped with several vascular dilators. It could then be possible to decrease the number of exposals and decrease the use of nurse anaesthetists for cannula and catheter insertions in sick patients. By using "arterialized" blood (i.e., increased circulation due to heat, whereby a greater part of artery blood enters the vein vessel system), it is not necessary in certain cases to utilize artery punction, but it is possible to take samples from a peripheral vein. Artery punction is often associated with a greater risk for the patient than ordinary venipunction.

Thus, a thermal vascular dilator can be used in numerous ways in both practical medical care and research. It has its place at all levels of medical care and in specialities, not least in children's hospitals and psychiatric clinics where venipuncture presents special problems.

SUMMARY OF THE INVENTION

The object of the invention is to provide a device of the kind initially stated which, apart from the desirable thermal properties, enables a practical and simple handling and is comfortable for the patient.

BRIEF DESCRIPTION OF THE DRAWING

An exemplary embodiment of the invention will now be described with reference to the accompanying drawing, wherein.

DESCRIPTION OF PREFERRED EMBODIMENT

Figure 1:
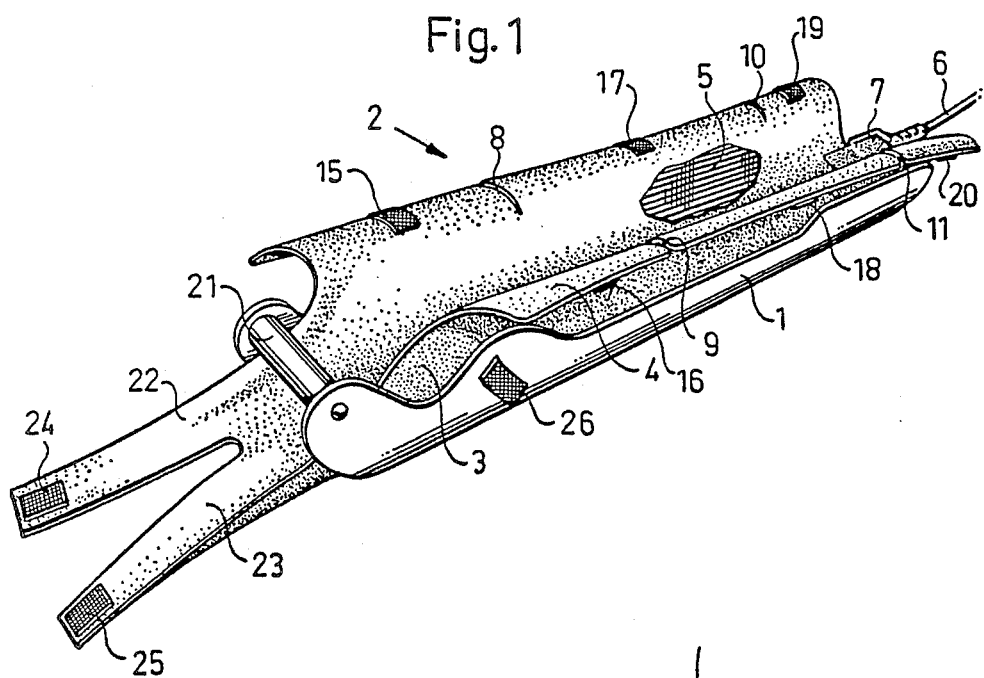
FIG. 1 is a perspective view of a thermal vascular dilator according to the invention and FIG. 2 shows the same with an arm of a patient received therein.

The thermal vascular dilator according to the invention comprises an elongate support member 1 of relatively rigid material, such as a hard plastic (thermoplastic resin). The support member 1 has the shape of a channel, substantially U-shaped in cross-section, which is adapted to the extremity in question, in this case an arm.

Inside the support member is fastened a sleeve 2 of flexible material, such as a relatively soft plastic. Between two layers 3 and 4 are laminated electrical resistance elements 5, which are voltage-fed through a cable 6 and a connection 7. Insulating layers (not shown) may be located between the elements 5 and the layers 3 and 4. The elements 5 preferably are so-called foil elements.

By means of slots 8, 9 and 10, 11 the sleeve 2 is divided into several sections 12, 13 and 14, which can be closed separately around the arm of a patient by superimposing opposed flaps of the sleeve portions on each other and interlocking them by cooperating so-called Velcro strips 15 and 16, 17 and 18, and, 19 and 20.

In the forward end of the support member 1 there is a cross-wise extending gripping handle 21, around which a patient is supposed to grip with his hand. Hereby is achieved what is achieved in normal venipunction by the patient clenching his hand, as well as a general stabilization of the entire aggregate relative to the arm of the patient.

In its forward end the sleeve 2 also has two forwardly directed flaps 22 and 23, which can be wrapped around the hand of the patient and fastened to the support member 1 onto Velcro strips attached thereon, only one (26) of which is shown in FIG. 1.

Figure 2:
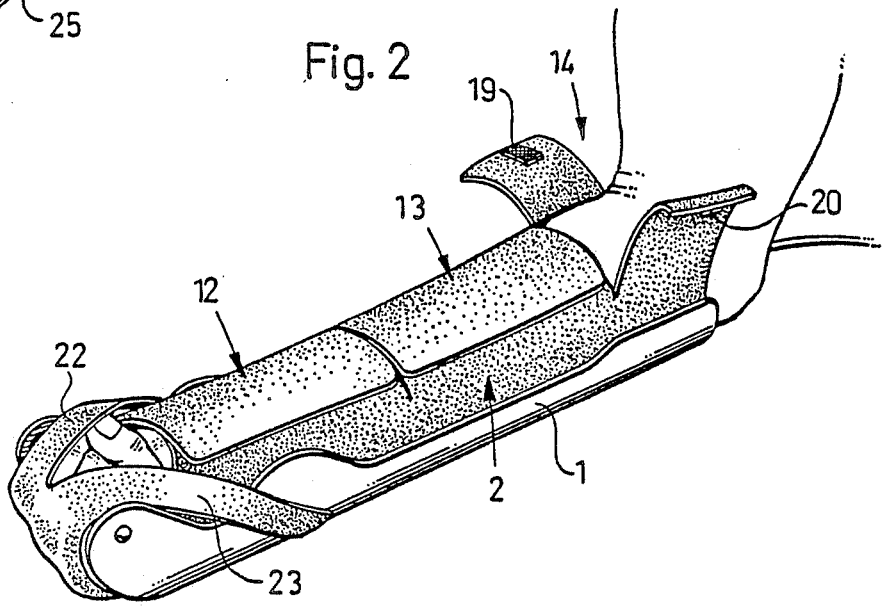

As appears from FIG. 2, after a desired heating time a certain section of the sleeve 2, here the section 14, may be opened for exposal of the arm of the patient.

I claim:

1. A device for dilating extremity blood vessels by thermal treatment, comprising a support member (1) of rigid material having a substantially U-shaped cross-section and adapted for receiving an extremity, a gripping handle (21) on said support member, and a sleeve (2) of flexible material arranged on the inside of the support member, said sleeve being adapted to be wrapped around an extremity received in the support member, said sleeve including heat emitting means (5).

2. A device according to claim 1, wherein said sleeve (2) is divided into several sections (12, 13, 14) separately wrappable around an extremity.

3. A device according to claim 1 or 2, wherein said sleeve (2) and sleeve sections (12, 13, 14), respectively, is/are adapted to be overlappingly wrapped around an extremity and to be locked in the wrapped state by means of hook and loop strips (15, 20).

4. A device according to claim 1, wherein said heat emitting means comprises electrical resistance elements (5).

5. A device according to claim 1, wherein said sleeve (2) has a portion (22, 23), which is adapted to be wrapped around the hand of an arm received in the support member (1).

* * * * *